United States Patent
Hodes et al.

(10) Patent No.: US 10,632,051 B2
(45) Date of Patent: Apr. 28, 2020

(54) HAIR BLEACHING AGENT AND METHOD FOR GENTLE OXIDATIVE LIGHTENING OF HAIR

(71) Applicant: Henkel AG & Co. KGaA, Duesseldorf (DE)

(72) Inventors: Jing Hodes, Hagen (DE); Daniela Kessler-Becker, Leverkusen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/215,838

(22) Filed: Dec. 11, 2018

(65) Prior Publication Data

US 2019/0175462 A1 Jun. 13, 2019

(30) Foreign Application Priority Data

Dec. 12, 2017 (DE) .................. 10 2017 222 516

(51) Int. Cl.
| | | |
|---|---|---|
| *A61Q 5/08* | (2006.01) | |
| *A61K 8/22* | (2006.01) | |
| *A61K 8/362* | (2006.01) | |
| *A61K 8/49* | (2006.01) | |
| *A61K 8/19* | (2006.01) | |
| *A61K 8/23* | (2006.01) | |
| *A61Q 5/10* | (2006.01) | |
| *A45D 19/00* | (2006.01) | |

(52) U.S. Cl.
CPC .................. *A61K 8/22* (2013.01); *A61K 8/19* (2013.01); *A61K 8/23* (2013.01); *A61K 8/362* (2013.01); *A61K 8/4973* (2013.01); *A61Q 5/08* (2013.01); *A61Q 5/10* (2013.01); *A45D 2019/0066* (2013.01); *A61K 2800/87* (2013.01); *A61K 2800/882* (2013.01)

(58) Field of Classification Search
None
See application file for complete search history.

(56) References Cited

U.S. PATENT DOCUMENTS

| | | |
|---|---|---|
| 6,206,935 B1 | 3/2001 | Onitsuka et al. |
| 9,980,891 B2 | 5/2018 | Manneck et al. |
| 2010/0162493 A1 | 7/2010 | Audousset et al. |
| 2011/0247644 A1 | 10/2011 | Oberkobusch et al. |
| 2017/0165161 A1* | 6/2017 | Manneck ............... A61Q 5/10 |
| 2017/0340549 A1* | 11/2017 | Anderheggen ...... A61K 8/0225 |
| 2019/0167548 A1* | 6/2019 | Goutsis ................. A61K 8/345 |

FOREIGN PATENT DOCUMENTS

| | | |
|---|---|---|
| DE | 10008640 | 8/2000 |
| DE | 102005013488 A1 | 9/2006 |
| DE | 102005017913 A1 | 10/2006 |
| DE | 102010063370 A1 | 6/2012 |
| EP | 1022014 A1 | 7/2000 |
| WO | 2005123020 A | 12/2005 |
| WO | 2017085117 A1 | 5/2017 |

* cited by examiner

*Primary Examiner* — Jyothsna A Venkat
(74) *Attorney, Agent, or Firm* — Lorenz & Kopf, LLP

(57) ABSTRACT

The subject matter of the present disclosure is the use of a combination of succinic acid and ethylene carbonate in a hair bleaching agent to reduce the damage to keratinic fibers due to the oxidative hair lightening.

10 Claims, No Drawings

HAIR BLEACHING AGENT AND METHOD FOR GENTLE OXIDATIVE LIGHTENING OF HAIR

CROSS-REFERENCE TO RELATED APPLICATION

This application claims priority to German Patent Application No. 10 2017 222 516.5, filed Dec. 12, 2017, which is incorporated herein by reference in its entirety.

TECHNICAL FIELD

The present disclosure relates to hair bleaching agents used as agents for lightening keratinic fibers, in particular human hair. In addition, the present disclosure relates to the use of these agents for gentle bleaching and/or oxidative lightening of human hair, a multicomponent package unit (kit of parts), comprising a plurality of separate components, which together form a hair bleaching agent for general oxidative lightening of keratinic fibers, as well as a method for oxidative lightening of keratinic fibers using the aforementioned hair bleaching agent, and the kit containing this hair bleaching agent.

BACKGROUND

Many consumers have long had the desire to lighten their hair color because a blond hair color is considered to be attractive and desirable from a fashion standpoint. For this purpose, various hair bleaching agents with different bleaching capabilities are available on the market. The oxidizing agents contained in these products are capable of lightening hair fibers by oxidative destruction of endogenous melanine pigment. For a moderate hair bleaching effect, it is sufficient to use hydrogen peroxide alone—optionally also with ammonia or other alkalizing agents—as the oxidizing agent. To achieve a stronger hair bleaching effect, a mixture of hydrogen peroxide and at least one compound selected from percarbonates and peracids, in particular peroxodisulfate salts and/or peroxomonosulfate salts, is used in general. To increase the hair bleaching effect, the agents contain greater use concentrations of hydrogen peroxide and percarbonates or peracids, in particular persulfates. Dark hair, dark brown hair or black hair can thus be lightened by four to six shades in one step. The hydrogen peroxide and the percarbonates or peracids are stored separately from one another until used, so as not to deactivate the percarbonates or peracids prematurely. The hydrogen peroxide component, comprising an aqueous solution of hydrogen peroxide, has an acidic pH to stabilize the hydrogen peroxide.

For the melanine-degrading effect of hydrogen peroxide and the hair bleaching effect on keratinic fibers, however, it is advantageous if the application mixture of hydrogen peroxide solution and persalt has an alkaline pH.

There are various possibilities to achieve an alkaline pH of the lightening application mixture:
The hair bleaching agent contains at least one powdered alkalizing agent in a total amount, such that the application mixture has the desired alkaline pH,
or
the hydrogen peroxide solution is additionally combined with an alkalizing agent preparation for the application mixture.

However, lightening of hair is also associated with damage to hair because there is oxidative damage not only to the hair pigment but also to the structural components of hair. Depending on the manifestation of the degree of damage, it ranges from coarse, brittle and difficult-to-comb-out hair to hair with a reduced resistance and tear strength or even to breakage of hair. The greater the amount of hydrogen peroxide and optional persalts or percarbonates used, even greater damage is therefore usually done to the keratin fibers.

Various methods have been used to minimize the damage to hair and to compensate for the damaging effect of the oxidizing agents.

EP 1022014 A1 describes an acidic hair coloring agent, which contains an alkylene carbonate and is optionally adjusted to an acidic pH with organic dicarboxylic acids. DE 102010063370 and DE 102005013488 disclose the use of solubilizers based on acylpyridinium derivatives to improve the lightening effect of hair bleaching agents, so that the required amount of damaging substances to be used can be reduced. DE 10008640 discloses a hair bleaching method under acidic conditions, which also reduces hair damage. However, the oxidizing agent is typically less reactive here than under alkaline conditions, so that the efficiency of the hair bleaching method can be limited. WO 2017/085117 discloses hair bleaching agents in which a gentle lightening of the hair is made possible with the addition of certain amino acids with dicarboxylic acids. Although good results are achieved even with the methods described here, there still remains a wide range for improvements.

BRIEF SUMMARY

Hair bleaching agents and used of the same, and methods of keratinic fiber lightening are provided. In an exemplary embodiment, a hair bleaching agent comprises a composition (A) with an alkalizing agent and an optional persalt, a composition (B) with hydrogen peroxide, and an optional composition (C) with a persalt. Composition (B) has a pH of from about 2.5 to about 5.5, and when all the compositions are mixed together the hair bleaching agent has an alkaline pH of from about 8 to about 12. The hair bleaching agent also comprises succinic acid and ethylene carbonate.

A method of lightening keratinic fibers is provided in another embodiment. The method includes combining all compositions of a hair bleaching agent, where the hair bleaching agent includes a composition (A), a composition (B), and an optional composition (C). Composition (A) comprises an alkalizing agent and an optional persalt, composition (B) comprises hydrogen peroxide, and optional composition (C) comprises a persalt. Composition (B) has a pH of from about 2.5 to about 5.5, and the hair bleaching agent also comprises succinic acid and ethylene carbonate. All the compositions are mixed, and the hair bleaching agent has an alkaline pH of from about 8 to about 12 after mixing. The hair bleaching agent is applied to keratinic fibers immediately after mixing and left on the keratinic fibers for from about 5 to about 60 minutes. The keratinic fibers are rinsed with water, and optionally washed with a cleaning agent comprising a surfactant.

A use of a hair bleaching agent is provided in yet another embodiment. A combination of succinic acid and ethylene carbonate are used in the hair bleaching agent to reduce damage to keratinic fibers during oxidative lightening. The hair bleaching agent comprises the succinic and the ethylene carbonate, as well as a composition (A), a composition (B), and an optional composition (C). Composition (A) comprises an alkalizing agent and an optional persalt, composition (B) comprises hydrogen peroxide, and optional composition (C) comprises a persalt. Composition (B) has a pH of from about 2.5 to about 5.5, and when all the compositions of the hair bleaching agent are mixed together an alkaline pH of from about 8 to about 12 is established.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide agents for lightening and/or bleaching keratinic fibers, in particular human hair, so as to cause the least possible damage to the keratin fibers while being easy to produce and handle.

The objects defined above are surprisingly achieved by adding a combination of succinic acid and ethylene carbonate to an alkaline hair bleaching agent. By adding succinic acid and ethylene carbonate to an agent for oxidative lightening of keratinic fibers, the investigators have succeeded in reducing damage to fibers in oxidative lightening without thereby having to avoid alkaline conditions and the associated quality of the lightening result. Combinations of ethylene carbonate with other acids as well as combinations of propylene carbonate with succinic acid or other acids have led either to greater damage to the keratinic fibers in comparison with the formulation as contemplated herein or to a visibly reduced lightening effect.

A first subject matter of the present disclosure is therefore a hair bleaching agent for lightening keratinic fibers, in particular human hair, containing:
a) a composition (A), containing at least one alkalizing agent and optionally at least one persalt; and
b) a composition (B) with a pH of from about 2.5 to about 5.5, preferably from about 3 to about 5, especially preferably from about 3.2 to about 4, containing hydrogen peroxide; and
c) optionally a composition (C), containing at least one persalt;
wherein, when all the components of the hair bleaching agent are mixed together, an alkaline pH is established, preferably in the range of from about 8 to about 12, especially from about 8.5 to about 11.5, especially preferably from about 9 to about 10.5,
exemplified in that the hair bleaching agent contains succinic acid and ethylene carbonate.

The hair bleaching agents as contemplated herein have good bleaching values with effective protection of keratinic fibers at the same time. They are also easy to produce and easy to handle.

Keratin-containing and/or keratinic fibers are understood to be furs, wool, feathers and in particular human hair. Although the agents as contemplated herein are suitable primarily for oxidative lightening of keratin-containing fibers, there is in principle nothing against their use in other fields as well.

A suitable parameter for quantification of fiber damage, in particular damage to hair, is the measurement of the cystic acid content of the keratin fibers which is elevated in oxidation of the cysteine groups contained in keratin fibers.

The term "powder" or "powdery" is understood to refer to a composition of individual particles that is solid and free-flowing at about 20° C. and about 1013 mbar and in which the individual particles have particle sizes in the range of from about 0.1 µm to a max. of about 1.6 mm. The particle sizes can preferably be determined by employing laser diffraction measurement according to ISO 13320-1 (2009). The particle size of the particles may optionally be adapted to the requirements of the hair bleaching agent by employing physical treatments such as screening, pressing, granulation or pelletizing or by adding certain additives to facilitate mixing of the individual powder ingredients or the miscibility of the hair bleaching agent with a hydrogen peroxide preparation.

Powdered compositions preferred as contemplated herein have a bulk density in the range of from about 500 to about 1000 g/L (grams per liter), preferably from about 550 to about 900 g/L, especially preferably from about 600 to about 820 g/L. The bulk density is preferably determined according to EN ISO 60 (version 01/2000) or DIN ISO 697 (version 01/1984).

Unless otherwise indicated, all temperatures given are based on a pressure of about 1013 mbar.

The terms "paste" or "pasty" are understood to refer to a composition having a viscosity in the range of from about 200,000 to about 1,600,000 mPas, preferably from about 250,000 to about 1,400,000 mPas, especially preferably from about 300,000 to about 1,000,000 mPas, extremely preferably from about 400,000 to about 750,000 Pas at about 20° C. and about 1013 mbar.

The paste viscosity is preferably determined by employing Brookfield; RVDV II+ device; spindle no. 96, about 4 rpm at about 20° C.

The terms "cream" or "creamy" are understood to refer to a composition including mainly an oil-in-water emulsion or a water-in-oil emulsion with ingredients suspended or dissolved therein.

The terms "gel" or "gelatinous" are understood to refer to a composition including mainly an aqueous solution or an oil-in-water emulsion with ingredients suspended or dissolved therein and treated with a gelling agent.

Unless otherwise indicated, all pH values are measured at about 20° C. Percentage amounts refer to percent by weight, unless otherwise indicated.

In the context of the present patent application, the term "hair bleaching" refers to oxidative lightening of keratinic fibers, in particular human hair.

Hair bleaching agents as contemplated herein do not contain any oxidative dyes or their precursors. Direct dyes may optionally be present to mask unwanted hues but not to cause an independent coloration.

The hair bleaching agents as contemplated herein preferably do not contain any acylpyridinium derivatives.

The hair bleaching agent as contemplated herein contains a composition (A), a composition (B), optionally a composition (C) and optionally a composition (D), wherein (A), (B), (C) and (D) are separate from one another and wherein (A) contains at least one alkalizing agent and optionally at least one persalt, preferably a percarbonate or a persulfate, especially preferably a persulfate;
(B) contains hydrogen peroxide and has a pH of from about 2.5 to about 5.5, preferably of from about 3 to about 5, especially preferably of from about 3.2 to about 4; and
if (C) is present, (C) contains at least one persalt, preferably a percarbonate or a persulfate, especially preferably a persulfate;
wherein at least one of compositions (A) or (B) or optionally (C) or optionally (D) contains succinic acid and at least one of compositions (A) or (B) or optionally (C) or optionally (D) contains ethylene carbonate, and when compositions (A), (B), (C) and (D) are mixed, an alkaline pH is established, preferably in the range of from about 8 to about 12, especially preferably from about 8.5 to about 11.5, extremely preferably from about 9.0 to about 10.5, each measured at about 20° C.

In one embodiment, (A) is a cream or a gel with a high alkalizing agent content, preferably ammonia or monoethanolamine; (B) is an aqueous hydrogen peroxide solution or emulsion with a pH of from about 2.5 to about 5.5, preferably of from about 3 to about 5, especially preferably of from about 3.2 to about 4, (D) is an aqueous solution of succinic acid and ethylene carbonate and (C) is not present.

In a second embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4, (C) and (D) are not present, wherein either (A) or (B) contains both succinic acid and ethylene carbonate.

In a third embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4, (C) and (D) are not present, wherein (A) contains a component selected from succinic acid and ethylene carbonate and (B) contains the component selected from succinic acid and ethylene carbonate that is not contained in (A).

In a fourth embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4; (C) is a powder containing persalt, preferably a powder containing a persulfate or percarbonate, especially preferably a powder containing a persulfate, optionally containing a filler, preferably silica, optionally containing an oil and optionally containing a powdered alkalizing agent; and (D) contains an aqueous solution of succinic acid and ethylene carbonate.

In a fifth embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4; (C) is a powder containing persalt, preferably a powder containing a persulfate or percarbonate, especially preferably a powder containing a persulfate, optionally containing a filler, preferably silica, optionally containing an oil and optionally containing a powdered alkalizing agent; and (D) is not present, wherein either (A) or (B) or (C) contains both succinic acid and ethylene carbonate.

In a sixth embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4; (C) is a powder containing persalt, preferably a powder containing a persulfate or percarbonate, especially preferably a powder containing a persulfate, optionally containing a filler, preferably silica, optionally containing an oil and optionally containing a powdered alkalizing agent; and (D) is not present, wherein either (A) or (C) contains a component selected from succinic acid and ethylene carbonate, and (B) contains the component selected from succinic acid and ethylene carbonate not contained in (A) or (C).

In a seventh embodiment, (A) is a cream or a gel with a high alkalizing agent content, preferably ammonia or monoethanolamine, (B) is an aqueous hydrogen peroxide solution or emulsion with a pH of from about 2.5 to about 5.5, preferably of from about 3 to about 5, especially preferably of from about 3.2 to about 4; (C) is a powder containing persalt, preferably a powder containing a persulfate or percarbonate, especially preferably a powder containing a persulfate, optionally containing a filler, preferably silica, optionally containing an oil and optionally containing a powdered alkalizing agent; and (D) is not present, wherein (A) contains a component selected from succinic acid and ethylene carbonate, and (C) contains the component selected from succinic acid and ethylene carbonate not contained in (A).

In an eighth embodiment, (A) is a powder or an anhydrous oil paste with a high alkalizing agent content, preferably an alkali sulfate, additionally containing at least one persalt, preferably a persulfate or a percarbonate, especially preferably a persulfate; (B) is an aqueous hydrogen peroxide solution or emulsion with a pH of from about 2.5 to about 5.5, preferably of from about 3 to about 5, especially preferably from about 3.2 to about 4; (D) contains an aqueous solution of succinic acid and ethylene carbonate and (C) is not present.

In a ninth embodiment, (A) is a powder or an anhydrous oil paste with a high alkalizing agent content, preferably an alkali sulfate, additionally containing at least one persalt, preferably a persulfate or a percarbonate, especially preferably a persulfate; (B) is an aqueous hydrogen peroxide solution or emulsion with a pH of from about 2.5 to about 5.5, preferably of from about 3 to about 5, especially preferably from about 3.2 to about 4; and (C) and (D) are not present, wherein either (A) or (B) contains both succinic acid and ethylene carbonate.

In a tenth embodiment, (A) is a powder or an anhydrous oil paste with a high alkalizing agent content, preferably an alkali sulfate, additionally containing at least one persalt, preferably a persulfate or a percarbonate, especially preferably a persulfate; (B) is an aqueous hydrogen peroxide solution or emulsion with a pH of from about 2.5 to about 5.5, preferably of from about 3 to about 5, especially preferably from about 3.2 to about 4; and (C) and (D) are not present, wherein (A) contains a component selected from succinic acid and ethylene carbonate, and (B) contains the component that is selected from succinic acid and ethylene carbonate but is not contained in (A).

A high alkalizing agent content is understood to refer to a content in which mixing the compositions (A), (B) and optionally (C) and optionally (D) results in an alkaline pH, preferably in the range of from about 8 to about 12, especially preferably from about 8.5 to about 11.5, extremely preferably from about 9.0 to about 10.5.

The aforementioned embodiments are given only as examples of embodiments, and the present disclosure is not limited to these embodiments.

Individual components and the compositions (A), (B), (C) and (D) are described in greater detail below.

Succinic Acid and Ethylene Carbonate

Hair bleaching agents as contemplated herein contain both succinic acid and ethylene carbonate, wherein these are distributed in any among the compositions (A), (B), optionally (C) and optionally (D).

Preferred hair bleaching agents as contemplated herein contain succinic acid in a single composition selected from (A), (B), optionally (C) and optionally (D) and ethylene carbonate in a single composition selected from (A), (B), optionally (C) and optionally (D). The succinic acid may be contained in the same composition as the ethylene carbonate or in a different composition than the ethylene carbonate.

In a preferred embodiment, succinic acid and ethylene glycol form a separate composition (D).

In a preferred embodiment, the composition (A) contains succinic acid and ethylene carbonate.

In another preferred embodiment, composition (A) contains succinic acid and composition (B) contains ethylene carbonate.

In another preferred embodiment, composition (A) contains ethylene carbonate and composition (B) contains succinic acid.

In another preferred embodiment, the hair bleaching agent as contemplated herein contains a composition (C), and succinic acid is in composition (C) and ethylene carbonate is in composition (B).

In another preferred embodiment, the hair bleaching agent as contemplated herein contains a composition (C), and succinic acid is in composition (C) and ethylene carbonate is in composition (A).

In another preferred embodiment, the hair bleaching agent as contemplated herein contains a composition (C), and succinic acid is in composition (B) and ethylene carbonate is in composition (C).

In another preferred embodiment, the hair bleaching agent as contemplated herein contains a composition (C), and succinic acid is in composition (A) and ethylene carbonate is in composition (C).

Preferred hair bleaching agents as contemplated herein contain between from about 0.01% by weight to about 1% by weight, preferably between from about 0.1% by weight to about 0.8% by weight, especially preferably between from about 0.2 to about 0.5% by weight, extremely preferably between from about 0.3 to about 0.4% by weight succinic acid and between from about 0.01% by weight to about 1% by weight, preferably between from about 0.1% by weight to about 0.8% by weight, especially preferably between from about 0.2 to about 0.5% by weight, extremely preferably between from about 0.3 to about 0.4% by weight ethylene carbonate, each based on the weight of the total bleaching agent.

Especially preferred hair bleaching agents as contemplated herein contain succinic acid and ethylene carbonate in a weight-based ratio of succinic acid to ethylene carbonate of from about 3:1 to about 1:3, preferably of from about 2:1 to about 1:2, especially preferably of from about 1.5:1 to about 1:1.5, extremely preferably about 1:1.

One subject matter of the present disclosure is also the use of a combination of succinic acid and ethylene carbonate in an alkaline hair bleaching agent to reduce the damage to keratinic fibers, in particular human hair, in oxidative lightening of these fibers, wherein the hair bleaching agent is preferably a hair bleaching agent as contemplated herein.

Composition (A)

Hair bleaching agents as contemplated herein contain in composition (A) at least one alkalizing agent. If composition (A) is in the form of a cream or lotion, the alkalizing agent is preferably selected from ammonia and amines, wherein the amine is preferably an alkanolamine, especially preferably monoethanolamine, 2-amino-2-methylpropanol and triethanolamine, most especially preferably monoethanolamine.

In preferred hair bleaching agents as contemplated herein, containing as the alkalizing agent ammonia or an amine, preferably ammonia or monoethanolamine, especially preferably ammonia in composition (A), composition (A) contains water and has a pH in the range of from about 8 to about 12, preferably of from about 9 to about 11, especially preferably of from about 9.5 to about 10.5, each measured at about 20° C. Ammonia ($NH_3$) is generally used in the form of its aqueous solution. Aqueous ammonia solutions often contain ammonia ($NH_3$) in concentrations of from about 10 to about 32% by weight. Use of an aqueous ammonia solution containing about 25% by weight ammonia ($NH_3$) is preferred here.

Ammonia and/or monoethanolamine are preferably contained in the alkalizing agent compositions preferably used as contemplated herein, in amounts of from about 0.01 to about 10% by weight, preferably from about 0.1 to about 7.5% by weight, more preferably from about 0.5 to about 5.5% by weight and especially preferably from about 1.5 to about 4.5% by weight, each based on the weight of the composition (A).

In addition to ammonia and alkanolamines, at least one other alkalizing agent may be present, selected from alkali metal silicates, alkaline earth metal silicates, alkaline earth metal hydroxycarbonates, alkaline earth metal carbonates, alkali metal metasilicates, alkaline earth metal metasilicates, alkali metal hydroxides and alkaline earth metal hydroxides as well as mixtures of these substances.

Hair bleaching agents as contemplated herein, in which composition (A) is present as a powder or anhydrous oil paste, preferably contain only solid alkalizing agents (at about 20° C. and about 1013 mbar), preferably selected from the substances listed above.

In a preferred embodiment, hair bleaching agents as contemplated herein optionally contain at least one persalt as an oxidizing agent in composition (A).

Examples of persalts as contemplated herein include percarbonates and persulfates. Percarbonates are understood in particular to be sodium carbonate-hydrogen peroxide complexes. Commercially available sodium percarbonate has the average composition $2Na_2CO_3 \cdot 3H_2O_2$. Sodium percarbonate is in the form of a white, water-soluble powder, which disintegrates readily into sodium carbonate and "active" oxygen that has a bleaching and oxidizing effect. Persulfates are understood to be the inorganic salts of peroxosulfuric acids. Peroxosulfuric acids are understood to be peroxodisulfuric acid and peroxomonosulfuric acid (Caro's acid). The persulfates are preferably selected from ammonia peroxodisulfate, alkali metal peroxodisulfate, ammonium peroxomonosulfate, alkali metal peroxomonosulfates and alkali metal hydrogen peroxomonosulfates. Ammonium peroxodisulfate, potassium peroxodisulfate, sodium peroxodisulfate and potassium hydrogen peroxomonosulfate are especially preferred. In a preferred embodiment, the hair bleaching agent as contemplated herein contains at least two different peroxodisulfates. Preferred peroxodisulfate salts here are combinations of ammonium peroxodisulfate and potassium peroxodisulfate and/or sodium peroxodisulfate.

The at least one persalt is preferably selected from sodium percarbonates and inorganic salts of a peroxosulfuric acid as well as mixtures thereof in a total amount of from about 5% to about 85% by weight, preferably from about 10% to about 75% by weight, especially preferably from about 15% to about 65% by weight, extremely preferably from about 20% to about 55% by weight, each based on the weight of the composition (A).

Hair bleaching agents as contemplated herein containing only solid alkalizing agents, preferably at least one alkali silicate, in composition (A), preferably also contain an oxidizing agent selected from sodium percarbonates and inorganic salts of a peroxosulfuric acid as well as mixtures thereof in a total amount of from about 5 to about 85% by weight, preferably from about 10 to about 75% by weight, especially preferably from about 15 to about 65% by weight, extremely preferably from about 20 to about 55% by weight, each based on the weight of composition (A).

Preferred hair bleaching agents as contemplated herein containing in composition (A) an oxidizing agent selected from sodium percarbonates and inorganic salts of a peroxosulfuric acid as well as mixtures thereof, additionally contain in composition (A) at least one inorganic alkalizing agent that is solid at about 20° C. and about 1013 mbar, including at least one sodium silicate or sodium metasilicate with a molar $SiO_2/Na_2O$ ratio of $\geq 2$, preferably from about 2.5 to about 3.5 in a total amount of from about 0.1 to about 50% by weight, preferably from about 5 to about 40% by weight, each based on the weight of composition (A). The alkalizing agent, which is solid at about 20° C. and about 1013 mbar is preferably present in a total amount of from about 1 to about 60% by weight, preferably from about 5 to about 55% by weight, especially preferably from about 10 to about 50% by weight, extremely preferably from about 15 to about 45% by weight, based on the weight of composition (A). In addition to the at least one sodium silicate or sodium metasilicate with a molar $SiO_2/Na_2O$ ratio of $\geq 2$, preferably from about 2.5 to about 3.5, in a total amount of from about 0.1 to about 50% by weight, preferably from about 5 to about 40% by weight, each based on the weight of composition (A) additional inorganic alkalizing agents that are solid at about 20° C. and about 1013 mbar and are most especially preferred as contemplated herein are selected from alkaline earth metal silicates, alkaline earth metal hydroxycarbonates, alkaline earth metal carbonates, alkaline earth metal metasilicates, alkali metal hydroxides, alkaline earth metal hydroxides, alkaline (earth) metal phosphates and alkaline (earth) metal hydrogen phosphates as well as mixtures of these substances. In addition to the at least one obligatory sodium silicate or sodium metasilicate, each with a molar $SiO_2/Na_2O$ ratio of $\geq 2$, preferably from about 2.5 to about 3.5, especially preferred inorganic alkalizing agents that are solid at about 20° C. and about 1013 mbar as contemplated herein are selected from magnesium hydroxycarbonates and mixtures of these alkalizing agents. Preferred magnesium hydroxycarbonates as contemplated herein are those with the formula $MgCO_3.Mg(OH)_2.2H_2O$ and those with the formula $MgCO_3.Mg(OH)_2$. Magnesium hydroxycarbonate with the formula $MgCO_3.Mg(OH)_2$ is especially preferred as contemplated herein.

Especially preferred hair bleaching agents as contemplated herein, which contain in composition (A) an oxidizing agent selected from sodium percarbonates and inorganic salts of a peroxosulfuric acid as well as mixtures thereof, contain in composition (A), based on their total weight, from about 0.1% to about 50% by weight, preferably from about 5% to about 40% by weight sodium silicates with a molar $SiO_2/Na_2O$ ratio of $\geq 2$, preferably of from about 2.5 to about 3.5 and from about 2% to about 20% by weight, preferably from about 5% to about 15% by weight, especially preferably from about 8% to about 25% by weight magnesium hydroxycarbonate as the inorganic alkalizing agent solid at about 20° C. and about 1013 mbar.

Extremely preferred hair bleaching agents as contemplated herein contain in composition (A) in the absence of a composition (C), if present, each based on its total weight, from about 0.1% to about 50% by weight, preferably from about 5% to about 40% by weight sodium silicates with a molar $SiO_2/Na_2O$ ratio of $\geq 2$, preferably of from about 2.5 to about 3.5, and from about 2 to about 20% by weight, preferably from about 5 to about 15% by weight, especially preferably from about 10 to about 13% by weight magnesium hydroxycarbonate with the formula $MgCO_3.Mg(OH)_2$ as the inorganic alkalizing agent that is solid at about 20° C. and about 1013 mbar.

If the hair bleaching agent as contemplated herein or the hair bleaching agent preferred as contemplated herein contains one or more inorganic carbonates in composition (A), whether it is present as an alkalizing agent or as an oxidizing agent in the form of sodium carbonate-hydrogen peroxide complexes, then its content is preferably selected so that, in the application mixture with composition (B), optionally with composition (C) and optionally with composition (D), the total molar $CO_3^{2-}$ concentration amounts to at least about 0.015 mol/100 g of the application mixture.

If the hair bleaching agent as contemplated herein or the hair bleaching agent preferred as contemplated herein contains in composition (A) one or more inorganic carbonates, whether as the alkalizing agent or as the oxidizing agent in the form of sodium carbonate-hydrogen peroxide complexes, then its amount is especially preferably selected so that the total molar $CO_3^{2-}$ concentration in the application mixture with composition (B) and optionally with composition (D) is mathematically at least four times greater than the total concentration of proton donors.

If the hair bleaching agent as contemplated herein or the hair bleaching agent preferred as contemplated herein contains in composition (A) one or more inorganic carbonates, whether as an alkalizing agent or as an oxidizing agent in the form of sodium carbonate-hydrogen peroxide complexes, then its content is extremely preferably selected so that the total molar $CO_3^{2-}$ concentration in the application mixture with composition (B), optionally with composition (C) and optionally with composition (D) amounts to at least about 0.015 mol/100 g of the application mixture and is mathematically four times greater than the total concentration of proton donors.

The hair bleaching agents as contemplated herein preferably have a water content of from about 0 to about 8% by weight, preferably from about 0.1 to about 5% by weight, especially preferably from about 0.5 to about 3% by weight water in composition (A), based on the weight of composition (A) if this contains alkali silicates and not ammonia or an amine as the alkalizing agent.

These values are based on the free water content. The molecularly bound water content or the water of crystallization, which may be present in individual powder constituents is not taken into account here. The water content can be determined in accordance with ISO 4317 (version 2011-12) by employing Karl Fischer titration, for example.

To remove dust from composition (A) if it contains alkali silicates as the alkalizing agent and not ammonia or an amine, at least one dedusting agent, which is selected in particular from at least one oil, in particular from paraffin oil, silicone oil or ester oils as well as mixtures of these oils, may be added. The at least one oil is preferably present in a total amount of from about 0.1 to about 15% by weight, preferably from about 0.5 to about 10% by weight, especially preferably from about 1 to about 8% by weight, extremely preferably from about 2 to about 6% by weight, each based on the weight of the hair bleaching agent (A).

Oils preferred as contemplated herein are selected from natural and synthetic hydrocarbons, especially preferably from paraffin oils, $C_{18}$-$C_{30}$ isoparaffins, in particular isoeicosane, polyisobutenes and polydecenes additionally selected from $C_8$-$C_{16}$ isoparaffins, in particular from isodecane, isododecane, isotetradecane and isohexadecane as well as mixtures thereof as well as 1,3-di-(2-ethylhexyl) cyclohexane.

Additional oils that are preferred as contemplated herein are selected from the benzoic acid esters of linear or branched $C_{8-22}$ alkanols. Benzoic acid $C_{12}$-$C_{15}$ alkyl esters are especially preferred. Additional oils preferred as contemplated herein are selected from fatty alcohols with from 6 to about 30 carbon atoms, which are unsaturated or branched and saturated or branched and unsaturated. Preferred alcohols are 2-hexyldecanol, 2-octyldodecanol, 2-ethylhexyl alcohol and isostearyl alcohol.

Additional cosmetic oils preferred as contemplated herein are selected from the triglycerides (=triple esters of glycerol) of linear or branched saturated or unsaturated optionally hydroxylated $C_{8-30}$ fatty acids. Use of natural oils may be especially preferred, for example, amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazel nut oil, elderberry oil, black currant seed oil, jojoba oil, linseed oil, macadamia nut oil, corn germ oil, almond oil, marula oil, evening primrose oil, olive oil, palm oil, palm kernel oil, Brazil nut oil, pecan oil, peach kernel oil, rapeseed oil, castor oil, sea buckthorn pulp oil, sea buckthorn kernel oil, sesame oil, soy oil, sunflower oil, grapeseed oil, walnut oil, wild rose oil, wheat germ oil and the liquid fractions of coconut oil and the like. However, synthetic triglyceride oils, in particular capric/caprylic triglycerides, are also preferred.

Additional cosmetic oils that are especially preferred as contemplated herein are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexylsuccinate and di-(2-hexyldecyl)succinate.

Additional cosmetic oils that are especially preferred as contemplated herein are selected from the esters of the linear or branched, saturated or unsaturated fatty oils with from 2 to about 30 carbon atoms with linear or branched saturated or unsaturated fatty acids with from 2 to about 30 carbon atoms, which may be hydroxylated. These preferably include 2-hexyldecyl stearate, 2-hexyldecyl laurate, isodecyl neopentanoate, isononyl isononanoate, 2-ethylhexyl palmitate and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate and ethylene glycol dipalmitate.

Additional cosmetic oils that are preferred as contemplated herein are selected from the addition products of from 1 to 5 propylene oxide units onto monovalent or polyvalent $C_{8-22}$ alkanols, such as octanol, decanol, decanediol, lauryl alcohol, myristyl alcohol and stearyl alcohol, e.g., PPG-2-myristyl ether and PPG-3-myristyl ether. Additional cosmetic oils preferred as contemplated herein are selected from the addition products of at least six ethylene oxide units and/or propylene oxide units onto monovalent or polyvalent $C_{3-22}$ alkanols, such as glycerol, butanol, butanediol, myristyl alcohol and stearyl alcohol, which may be esterified, if desired, for example, PPG-14-butyl ether, PPG-9-butyl ether, PPG-10-butanediol, PPG-15-stearyl ether and glycereth-7-diisononanoate.

Additional cosmetic oils preferred as contemplated herein are selected from the $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid and salicylic acid, e.g., $C_{12}$-$C_{15}$ alkyl lactate.

Additional cosmetic oils preferred as contemplated herein are selected from the symmetrical, asymmetrical or cyclic esters of carbonic acid with $C_{3-22}$ alkanols, $C_{3-22}$ alkanediols or $C_{3-22}$ alkanetriols, e.g., dicaprylyl carbonate or the esters according to DE 19756454 A1, in particular glycerol carbonate.

Additional cosmetic oils suitable as contemplated herein are selected from the silicone oils, including for example dialkyl siloxanes and alkylaryl siloxanes such as decamethylcyclopentasiloxane, dodecamethylcyclohexasiloxane, dimethylpolysiloxane and methyl phenyl polysiloxane for example but also hexamethyldisiloxane, octamethyltrisiloxane and decamethyltetrasiloxane.

It may also be extremely preferable as contemplated herein to use mixtures of the aforementioned oils.

Preferred hair bleaching agents as contemplated herein are exemplified in that the cosmetic oil is selected from natural and synthetic hydrocarbons, especially preferably from paraffin oils, $C_{18}$-$C_{30}$ isoparaffins, in particular isoeicosane, polyisobutenes and polydecenes, $C_8$-$C_{16}$ isoparaffins as well as 1,3-di-(2-ethylhexyl)cyclohexane; the benzoic acid esters of linear or branched $C_8$-$C_{22}$ alkanols; fatty alcohols with from 6 to about 30 carbon atoms, which are saturated or branched and saturated or branched and unsaturated; triglycerides of linear or branched, saturated or unsaturated, optionally hydroxylated $C_{8-30}$ fatty acids, in particular natural oils; the dicarboxylic acid esters of linear or branched $C_2$-$C_{10}$ alkanols; the esters of linear or branched saturated or unsaturated fatty alcohols with from 2 to about 30 carbon atoms with linear or branched saturated or unsaturated fatty acids with from 2 to about 30 carbon atoms, which may be hydroxylated; the addition products of from 1 to 5 propylene oxide units onto monovalent or polyvalent $C_{8-22}$ alkanols; the addition products of at least 6 ethylene oxide and/or propylene oxide units onto monovalent or polyvalent $C_{3-22}$ alkanols; the $C_8$-$C_{22}$ fatty alcohol esters of monovalent or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$ fatty acids (dimer fatty acids) with monovalent linear branched or cyclic $C_2$-$C_{18}$ alkanols or with polyvalent linear or branched $C_2$-$C_6$ alkanols; silicone oils as well as mixtures of the aforementioned substances and preferably in a total amount of from about 0.1 to about 15% by weight, preferably from about 0.5 to about 10% by weight, especially preferably from about 1 to about 8% by weight, extremely preferably from about 2 to about 6% by weight, each based on the weight of the hair bleaching agent.

Preferred hair bleaching agents as contemplated herein may optionally contain at least one polymer selected from acrylic acid homo- and copolymers, methacrylic acid homo- and copolymers, itaconic acid homo- and copolymers, polysaccharides which may be modified chemically and/or physically, and blends of these polymers, wherein especially preferably one or more of the aforementioned polymers are present in a total amount of from about 0.1 to about 6% by weight, preferably from about 0.5 to about 4% by weight, especially from about 1 to about 3.5% by weight, extremely preferably from about 2 to about 3% by weight each based on the weight of the hair bleaching agent.

Composition (A) may optionally also contain in a preferred embodiment 2-[2-hydroxy-3-(trimethylammonio) propoxy] ethylcellulose ether chloride. The 2-[2-hydroxy-3-(trimethylammonio)propoxy]ethylcellulose ether chloride is preferably present in a total amount of from about 0.01 to about 1.00% by weight, especially preferably from about 0.10 to about 0.60% by weight, more especially preferably from about 0.20 to about 0.48% by weight, extremely preferably from about 0.30 to about 0.47% by weight, each based on the weight of the hair bleaching agent.

In a preferred embodiment the composition (A) additionally contains at least one amino acid selected from arginine, lysine, histidine or at least one of the salts of these amino acids. Arginine is extremely preferred. Mixtures of arginine and lysine may be especially preferred according to the present disclosure. Suitable salts of arginine, lysine or histidine that are preferred as contemplated herein include the ammonium salts, alkali metal salts and alkaline earth metal salts, in particular the lithium, sodium, potassium, magnesium and calcium salts, also the hydrohalides, in particular the hydrochlorides as well as mixtures of these salts. Lysine hydrochloride is an amino acid salt that is especially preferred as contemplated herein. The amino acids suitable as contemplated herein, selected from arginine, lysine, histidine and salts thereof, may also contain water of crystallization.

Compositions (A) that are preferred as contemplated herein may include at least one amino acid selected from arginine, lysine, histidine or at least one salt of these amino acids in a total amount of from about 0.1 to about 7% by weight, converted to the weight of free amino acid, preferably from about 0.2 to about 5% by weight, especially preferably from about 0.5 to about 2.5% by weight, extremely preferably from about 1 to about 2% by weight, each based on the weight of composition (A).

Composition (B)

Composition (B) in the hair bleaching agent as contemplated herein contains from about 50 to about 96% by weight, preferably from about 70 to about 93% by weight, especially preferably from about 80 to about 90% by weight water and from about 0.5 to about 20% by weight hydrogen peroxide, each based on the weight of composition (B), and additionally containing at least one pH adjusted agent in an amount such that composition (B) has a pH in the range of from about 2.5 to about 5.5 in particular from about 3 to about 5 measured at about 20° C.

Composition (B) in the hair bleaching agent as contemplated herein contains essentially water and hydrogen peroxide. The concentration of the hydrogen peroxide is determined on the one hand by the statutory requirements and on the other hand by the desired effect. It amounts to from about 0.5 to about 20% by weight, preferably from about 3 to about 12% by weight, especially preferably from about 6 to about 9% by weight hydrogen peroxide (calculated as 100% $H_2O_2$), each based on the weight of composition (B).

Composition (B) in the hair bleaching agent as contemplated herein preferably has an acidic pH to stabilize the hydrogen peroxide, in particular a pH in the range of from about 2.5 to about 5.5, in particular from about 3 to about 5, measured at about 20° C. To stabilize the hydrogen peroxide, chelating agents, preservatives and/or buffer substances are also preferably included.

Hair bleaching agents especially preferred as contemplated herein additionally contain at least one oil and/or at least one fat component in composition (B) with a melting point in the range of from about 23 to about 110° C., preferably in a total amount of from about 0.1 to about 60% by weight, especially preferably from about 0.5 to about 40% by weight, extremely preferably from about 2 to about 24% by weight, each based on the weight of composition (B). The oils in composition (B) that are suitable for the preferred hair bleaching agents as contemplated herein are the same oils as those disclosed above as being suitable dedusting agents.

Fat components with a melting point in the range of from about 23 to about 110° C. preferably used as contemplated herein in composition (B) are selected from linear saturated 1-alkanols with from about 12 to about 30 carbon atoms, preferably in a total amount of from about 0.1 to about 8% by weight, especially preferably from about 3.0 to about 6.0% by weight, each based on the weight of composition (B). The at least one linear saturated 1-alkanol with from about 12 to about 30 carbon atoms is preferably selected from lauryl alcohol, myristyl alcohol, cetyl alcohol, stearyl alcohol, arachidyl alcohol and behenyl alcohol as well as mixtures of these 1-alkanols, especially preferably from cetyl alcohol, stearyl alcohol and cetyl alcohol/stearyl alcohol mixtures.

Preferred hair bleaching agents as contemplated herein additionally contain, each based on weight, at least one linear saturated 1-alkanol with from about 12 to about 30 carbon atoms in a total amount of from about 0.1 to about 8% by weight, preferably in a total amount of from about 2 to about 6% by weight, wherein at least one alkanol selected from cetyl alcohol, stearyl alcohol and cetyl alcohol/stearyl alcohol mixtures is included.

Additional preferred compositions (B) as contemplated herein contain at least one fat component with a melting point in the range of from about 23 to about 110° C., selected from esters of a saturated monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which may be hydroxylated, candelilla wax, carnauba wax, beeswax, saturated linear $C_{14}$-$C_{36}$ carboxylic acids as well as mixtures of the aforementioned substances.

Additional preferred hair bleaching agents as contemplated herein contain in composition (B) at least one surfactant or at least one emulsifier, preferably in a total amount of from about 0.5 to about 10% by weight, preferably from about 1 to about 5% by weight, each based on the weight of composition (B). Surfactants and emulsifiers in the sense of the present disclosure include amphiphilic (bifunctional) compounds including at least one hydrophobic molecule part and at least one hydrophilic molecule part. The hydrophobic radical is preferably a hydrocarbon chain with from about 8 to about 28 carbon atoms, which may be saturated or unsaturated, linear or branched. This $C_8$-$C_{28}$ alkyl chain is especially preferably linear. Basic properties of the surfactants and emulsifiers are the oriented absorption on interfaces as well as the aggregation to micelles and the formation of lyotrophic phases.

As contemplated herein, anionic, nonionic and cationic surfactants are especially suitable. However, zwitterionic and amphoteric surfactants are also very suitable as contemplated herein.

All the anionic surfactants that are suitable for use on the human body are suitable as the anionic surfactants in the compositions as contemplated herein. These surfactants are exemplified by a water-solubilizing anionic group such as for example a carboxylate, sulfate, sulfonate or phosphate group and a lipophilic alkyl group with from about 8 to about 30 carbon atoms. In addition, glycol or polyglycol ether groups, ester, ether and amide groups as well as hydroxyl groups may also be included. Examples of suitable anionic surfactants are linear and branched fatty acids with from about 8 to about 30 carbon atoms (soaps), alkyl ether carboxylic acids, acyl sarcosides, acyl taurides, acyl isethionates, sulfosuccinic acid mono and dialkyl esters and sulfosuccinic acid monoalkylpolyoxyethyl esters, linear alkane sulfonates, linear α-olefin sulfonates, alkyl sulfates and alkyl ether sulfates as well as alkyl and/or alkenyl phosphates. Preferred anionic surfactants are alkyl sulfates, alkyl ether sulfates and alkyl ether carboxylic acids each with from about 10 to about 18 carbon atoms, preferably from about 12 to about 14 carbon atoms in the alkyl group and up to about 12 glycol ether groups, preferably from 2 to 6 glycol ether groups in the molecule. Examples of such surfactants include compounds with the INCI designations sodium laureth sulfate, sodium lauryl sulfate, sodium myreth sulfate or sodium laureth carboxylate.

Zwitterionic surfactants are surface-active compounds having at least one quaternary ammonium group and at least one carboxylate, sulfonate or sulfate group in the molecule. Especially suitable zwitterionic surfactants are the so-called betaines such as the N-alkyl-N,N-dimethylammonium glycinates, for example, cocoalkyldimethylammonium glycinate, N-acylaminopropyl-N,N-dimethylammonium glycinates, for example, cocoacylaminopropyldimethylammonium glycinate and 2-alkyl-3-carboxymethyl-3-hydroxyethylimidazolines, each with from about 8 to about 18 carbon atoms in the alkyl or acyl group as well as cocoacylaminoethylhydroxyethylcarboxymethyl glycinate. A preferred zwitterionic surfactant is the fatty acid amide derivative known by the INCI designation cocamidopropyl betaine.

Amphoteric surfactants are understood to be surface-active compounds, which have at least one free amino group and at least one —COOH or —SO$_3$H group in the molecule in addition to a $C_8$-$C_{24}$ alkyl or acyl group and which are capable of forming internal salts. Examples of suitable amphoteric surfactants include N-alkylglycines, N-alkylpropionic acids, N-alkylaminobutyric acids, N-alkyliminodipropionic acids, N-hydroxyethyl-N-alkylamidopropylglycine, N-alkyltaurines, N-alkylsarcosines, 2-alkylaminopropionic acids and alkylaminoacetic acids, each with from about 8 to about 24 carbon atoms in the alkyl group. Especially preferred amphoteric surfactants include N-cocoalkylaminopropionate, cocoacylaminoethylaminopropionate and $C_{12}$-$C_{18}$ acyl sarcosine. Nonionic surfactants contain as the hydrophilic group for example a polyol group, a polyalkylene glycol ether group or a combination of a polyol group and a polyglycol ether group. Such compounds include, for example, addition products of from about 4 to about 50 mol ethylene oxide and/or from about 0 to about 5 mol propylene oxide onto linear and branched fatty alcohols, fatty acids and alkylphenols, each with from about 8 to about 20 carbon atoms in the alkyl group, ethoxylate mono-, di- and triglycerides such as for example glycerol monolaurate+ 20 ethylene oxide and glycerol monostearate+20 ethylene oxide, sorbitan fatty acid esters and addition products of ethylene oxide onto sorbitan fatty acid esters such as the polysorbates (Tween 20, Tween 21, Tween 60, Tween 61, Tween 81), addition products of ethylene oxide onto fatty acid alkanolamides and fatty amines as well as alkyl polyglycosides. Suitable nonionic surfactants include in particular $C_8$-$C_{22}$ alkyl mono- and oligoglycosides and their ethoxylated analogs as well as ethylene oxide addition products onto saturated or unsaturated linear fatty alcohols each with from about 2 to about 30 mol ethylene oxide per mol fatty alcohol.

Additional preferred hair bleaching agents as contemplated herein are exemplified in that the at least one anionic surfactant in composition (B) is selected from alkyl sulfates, alkyl ether sulfates and alkyl ether carboxylic acids, each with from about 10 to about 18 carbon atoms, preferably from about 12 to about 14 carbon atoms in the alkyl group and up to about 12, preferably from 2 to 6 glycol ether groups, in the molecule.

Additional preferred hair bleaching agents as contemplated herein are exemplified in that at least one nonionic surfactant selected from ethylene oxide addition products onto saturated or unsaturated linear fatty alcohols, each with from about 2 to about 30 mol ethylene oxide per mol fatty alcohol, and at least one anionic surfactant selected from alkyl sulfates, alkyl ether sulfates and alkyl ether carboxylic acids, each with from about 10 to about 18 carbon atoms, preferably from about 12 to about 14 carbon atoms in the alkyl group and up to about 12, preferably from 2 to 6, glycol ether groups in the molecule, are present in composition (B), wherein the weight ratio of the totality of all anionic surfactants to the totality of all nonionic surfactants is especially preferably in the range of from about 5 to about 50 preferably from about 10 to about 30.

Suitable cationic surfactants in composition (B) of the hair bleaching agent preferred as contemplated herein include in principle all cationic surfactants suitable for use on the human body. These are exemplified by at least one water-solubilizing cationic group, for example a quaternary ammonium group, or by at least one water-solubilizing cationizable group, for example an amine group, and additionally at least one (lipophilic acting) alkyl group with from 6 to about 30 carbon atoms or at least one (lipophilic acting) imidazole group or at least one (lipophilic acting) imidazylalkyl group.

Especially preferred hair bleaching agents as contemplated herein contain at least one cationic surfactant in composition (B), preferably selected from quaternary ammonium compounds with at least one $C_8$-$C_{24}$ alkyl group, esterquats and amidoamines each with at least one $C_8$-$C_{24}$ acyl group and mixtures thereof. Preferred quaternary ammonium compounds with at least $C_8$-$C_{24}$ alkyl group include ammonium halides, in particular chlorides and ammonium alkyl sulfates such as methosulfates or ethosulfates such as $C_8$-$C_{24}$ alkyltrimethylammonium chlorides, $C_8$-$C_{24}$ dialkyldimethylammonium chlorides and $C_8$-$C_{24}$ trialkylmethyl ammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride as well as the imidazolium compounds known by the INCI designations quaternium-27, quaternium-83, quaternium-87 and quaternium-91. The alkyl chains of the aforementioned surfactants preferably have from about 8 to about 24 carbon atoms.

Esterquats are cationic surfactants having at least one ester function as well as at least one quaternary ammonium group as structural elements and in addition at least one $C_8$-$C_{24}$ alkyl group or $C_8$-$C_{24}$ acyl group. Preferred esterquats are quaternated ester salts of fatty acids with triethanolamine, quaternated ester salts of fatty acids with diethanolalkylamines and quaternated ester salts of fatty acids with 1,2-dihydroxypropyldialkylamines. Such products are distributed under the brand names Stepantex®, Dehyquart® and Armocare®, for example. N,N-bis(2-palmitoyloxyethyl)dimethylammonium chloride, distearoylethyldimonium methosulfate and distearoylethylhydroxyethylmonium methosulfate are preferred examples of such esterquats.

The alkylamidoamines are usually produced by amidation of natural or synthetic $C_8$-$C_{24}$ fatty acids and fatty acid cuts with di-($C_1$-$C_3$)alkylaminoamines. Stearamidopropyldimethylamine is a compound from this substance group that is especially suitable as contemplated herein.

Especially preferred hair bleaching agents as contemplated herein contain in composition (B) at least one cationic surfactant in a total amount of from about 0.01 to about 5% by weight, preferably from about 0.1 to about 3% by weight, especially preferably from about 0.3 to about 2% by weight, each based on the weight of the composition (B).

Composition (C)

Hair bleaching agents as contemplated herein optionally contain a composition (C) comprising at least one persalt, wherein this is defined as indicated above.

Hair bleaching agents as contemplated herein preferably contain a composition (C) only if composition (A) does not contain an oxidizing agent selected from sodium percarbonates and inorganic salts of a peroxosulfuric acid as well as mixtures thereof.

The ingredients of composition (C) are selected from the ingredient that may be present in a composition (A) containing an oxidizing agent selected from sodium percarbonates and inorganic salts of a peroxosulfuric acid as well as mixtures thereof.

Especially preferred hair bleaching agents as contemplated herein which contain a composition (C) contain ammonia or an amine as an alkalizing agent in composition (A), preferably ammonia or monoethanolamine, especially preferably ammonia.

Composition (D)

Hair bleaching agents as contemplated herein optionally contain a composition (D) comprising succinic acid and/or ethylene carbonate and optionally water. A composition (D) is present only if none of compositions (A), (B) or (C) contains succinic acid or ethylene carbonate.

To mask unwanted color hues formed in hair bleaching, the hair bleaching agent as contemplated herein optionally contains, preferably in composition (A) or (C), at least one direct dye. These are dyes that are absorbed directly on the hair and do not require any oxidative process to form the color. For delustering unwanted residual color impressions produced by melanine degradation products, in particular in the reddish or bluish range, certain direct dyes of the complementary colors are especially preferably and are also present. Direct dyes are usually nitrophenylenediamines, nitroaminophenols, azo dyes, anthraquinones or indophenols. Direct dyes may be anionic, cationic or nonionic. The direct dyes are each preferably present in an amount of from about 0.001 to about 2% by weight based on the weight of the composition (A) or (C).

Preferred anionic direct dyes are compounds known by the international designations and/or brand names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic direct dyes are cationic triphenylmethane dyes, for example, Basic Blue 7, Basic Blue 26, Basic Violet 2 and Basic Violet 14, aromatic systems substituted with a quaternary nitrogen group such as, for example, Basic Yellow 57, Basic Red 76, Basic Blue 99, Basic Brown 16 and Basic Brown 17, cationic anthraquinone dyes such as HC Blue 16 (Bluequat B) as well as direct dyes containing a heterocycle having at least one quaternary nitrogen atom, in particular Basic Yellow 87, Basic Orange 31 and Basic Red 51. The cationic direct dyes distributed under the brand name Arianor are also preferred cationic direct dyes as contemplated herein. Suitable nonionic direct dyes include in particular nonionic nitro and quinone dyes and neutral azo dyes. Preferred nonionic direct dyes are the compounds known by the international designations and/or brand names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and their salts, 2-amino-6-chloro-4-nitrophenol, 4-ethylamino-3-nitrobenzoic acid and 2-chloro-6-ethylamino-4-nitrophenol, picramic acid and salts thereof, 2-amino-6-chloro-4-nitrophenol, 4-ethylamino-3-nitrobenzoic acid and 2-chloro-6-ethylamino-4-nitrophenol. Most especially preferred as contemplated herein is a combination of tetrabromophenol blue and Acid Red 92.

Hair bleaching agents as contemplated herein and agents for dyeing keratin-containing fibers may additionally contain colored pigments for coloring the bleaching agent that do not serve to color the keratin-containing fibers in the composition (A) or optionally composition (C). Colored pigments selected from commercially available colored pigments are preferred and are present in a total amount of from about 0.1 to about 1% by weight, preferably from about 0.2 to about 0.7% by weight, especially preferably from about 0.3 to about 0.5% by weight based on the weight of composition (A) or optionally composition (C).

Application Mixture

The hair bleaching agent is preferably formulated as contemplated herein, so that the mixture of composition (A) with (B) and optionally (C) and optionally (D) has a pH of from about 8 to about 12, preferably of from about 8.5 to about 11.5, especially preferably from about 9 to about 10.5, extremely preferably a pH of from about 9.5 to about 10.2, each measured at about 20° C.

The hair bleaching agent as contemplated herein is usually in the form of a multicomponent package unit (kit of parts).

Another subject matter of the present disclosure is therefore a multicomponent package unit (kit of parts) for lightening keratinic fibers, containing at least two components packaged separately from one another and exemplified in that
i) the first component (I) includes composition (A),
ii) the second component (II) includes composition (B),
optionally iii) an additional component (III) includes composition (C) and optionally iv) an additional component (IV) includes composition (D), wherein components (I) and (II)

in the absence of a component (III) are preferably present in a weight-based ratio (I):(II) of about 0.2-1, especially preferably about 0.3-0.8, more preferably about 0.4-0.7, extremely preferably about 0.5-0.6, and in the presence of a component (III) the components (I), (II) and (III) are present in a weight-based ratio (I):(II):(III) of about (2-3):(2-3):(0.7-1.3), especially preferably about (2.3-2.7):(2.3-2.7):(0.8-1.2), extremely preferably about 2:2:1. In particularly preferred multicomponent package units (kits of parts) as contemplated herein, a component (IV) is present, wherein the weight-based ratio (II):(IV) amounts to about 20-2 preferably about 15-5 especially preferably about 12-8.

A multicomponent package unit comprises a plurality of individual components, which are fabricated separately from one another, as well as a combined package of these components for example a folded box in which the components are each presented separately in different containers. The term "container" in the context of the present disclosure is understood to refer to an enclosure which is in the form of an optionally reclosable bottle, tube, can, bag, sachet or similar enclosure. There are no limits to the material of the enclosure as contemplated herein. However, enclosures made of glass or plastic are preferred.

In addition, the package unit may include application aids, such as combs, brushes or paint brushes, personal protective clothing, in particular disposable gloves, as well as instructions for use.

Another subject matter of the present disclosure is the use of a hair bleaching agent as contemplated herein for oxidative lightening of keratin-containing fibers, in particular human hair.

Another subject matter of the present disclosure is a method for oxidative lightening of keratin-containing fibers, in particular human hair, exemplified in that the compositions (A) and (B) and optionally (C) and optionally (D) are mixed together and applied to the keratin-containing fibers immediately thereafter, left on the fibers for from about 5 to about 60 minutes, and then the fibers are rinsed with water and optionally washed out with a cleaning agent containing a surfactant, wherein composition (A) and composition (B) in the absence of composition (C) are preferably mixed together in a weight-based ratio (A):(B) of about 0.2-1, especially preferably about 0.3-0.8, more preferably about 0.4-0.7, extremely preferably about 0.5-0.6, and in the presence of composition (C), compositions (A), (B) and (C) are mixed together in a weight-based ratio (A):(B):(C) of about (2-3):(2-3):(0.7-1.3), especially preferably about (2.3-2.7):(2.3-2.7):(0.8-1.2), extremely preferably about 2:2:1. In methods especially preferred as contemplated herein, composition (D) is present in the hair bleaching agent, in which the weight-based ratio (B):(D) amounts to about 20-2 preferably about 15-5 especially preferably about 12-8.

Another subject matter of the present disclosure is agents for dyeing keratin-containing fibers, in particular human hair. These agents are formulated essentially from the same components as the hair bleaching agents as contemplated herein but additionally contain at least one oxidative dye precursor, which alters the hair color or at least one direct dye in one of the components (A) or (B) or optionally (C) or optionally (D), preferably in (A) or (C), especially preferably in (A).

An additional subject matter of the present disclosure is therefore a method for dyeing keratinic fibers, in particular human hair, in which compositions (A), (B), (C) and optionally (D) of an agent that is preferred as contemplated herein for dyeing keratin-containing fibers in particular human hair are mixed together, then applied to the keratin-containing fibers immediately thereafter, left on the fibers for from about 5 to about 60 minutes and then the fibers are rinsed with water and optionally washed out with a surfactant-containing cleaning agent, wherein the compositions (A), (B) and (C) are preferably mixed together in a weight-based ratio (A):(B):(C) of about (2-3):(2-3):(0.7-1.3) especially preferably about (2.3-2.7):(2.3-2.7):(0.8-1.2), extremely preferably about 2:2:1.

The coloring agent is preferably formulated as contemplated herein so that the mixture of compositions (A), (B), (C) and optionally (D), i.e. the ready-to-use coloring agent, has an alkaline pH, preferably a pH of from about 8 to about 112, especially preferably a pH of from about 8.5 to about 11.5, extremely preferably a pH of from about 9.0 to about 10.5, each measured at about 20° C.

The ready-to-use agents for dyeing keratin-containing fibers, in particular human hair, preferably have a viscosity in the range of from about 15,000 to about 100,000 mPas, especially preferably from about 20,000 to about 85,000 mPas, each measured at about 20° C. with a Brookfield viscometer, model DV-II+, spindle 5, at a speed of about 4 rpm. A viscosity in this range allows easy application of the ready-to-use agent, on the one hand, and on the other hand, has flow behavior such that it guarantees a sufficiently long treatment time at the site of action on the keratinic fibers for this agent.

To facilitate the miscibility of compositions (A), (B), (C) and optionally (D) and also to improve the application properties of the resulting application mixture, the composition (A) preferably contains at least one surfactant in a total amount of from about 0.5 to about 10% by weight, preferably from about 2 to about 8% by weight, each based on its weight.

The suitable surfactants are selected from the same anionic, cationic, nonionic, amphoteric and zwitterionic surfactants and emulsifiers as those disclosed above as surfactants and emulsifiers suitable for composition (B).

Agents especially preferred for use as contemplated herein for dyeing keratin-containing fibers, in particular human hair, additionally contain at least one oil and/or at least one fat component in composition (A) having a melting point in the range of from about 23 to about 110° C., preferably in a total amount of from about 0.1 to about 60% by weight, especially preferably from about 0.5 to about 40% by weight, extremely preferably from about 2 to about 24% by weight, each based on the weight of composition (A). The suitable oils are the same oils as disclosed above as suitable dedusting agents.

Fat components having a melting point in the range of from about 23 to about 110° C. and preferred for use in composition (A) as contemplated herein are selected from linear saturated 1-alkanols with from about 12 to about 30 carbon atoms, preferably in a total amount of from about 0.1 to about 20% by weight, especially preferably from about 3 to about 15% by weight, extremely preferably from about 5 to about 10% by weight, each based on the weight of composition (A).

The at least one linear saturated 1-alkanol with from about 12 to about 30 carbon atoms, selected from lauryl alcohol, myristyl alcohol, cetyl alcohol, stearyl alcohol, arachidyl alcohol and behenyl alcohol as well as mixtures of these 1-alkanols, especially preferably cetyl alcohol, stearyl alcohol and cetyl alcohol/stearyl alcohol mixtures, is preferred.

Agents preferred as contemplated herein for dyeing keratin-containing fibers, in particular human hair, additionally contain in composition (A), each based on its weight at least one linear saturated 1-alkanol with from about 12 to about 30 carbon atoms in a total amount of from about 0.1 to about 20% by weight, preferably in a total amount of from about 3 to about 15% by weight, extremely preferably from about 5 to about 10% by weight, wherein at least 1-alkanol selected from cetyl alcohol, stearyl alcohol and cetyl alcohol/stearyl alcohol mixtures is present.

Additional agents preferred for use as contemplated herein for dyeing keratin-containing fibers, in particular human hair, contain in composition (A) at least one fat component with a melting point in the range of from about 23 to about 110° C. selected from esters of a saturated monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which may be hydroxylated, candelilla wax, carnauba wax, beeswax, saturated linear $C_{14}$-$C_{36}$ carboxylic acids as well as mixtures of the aforementioned substances.

In addition, the agents as contemplated herein or the agents preferred as contemplated herein for dyeing keratin-containing fibers in particular human hair, contain at least one oxidative dye precursor and/or a direct dye in composition (A) or (C).

The at least one oxidative dye precursor preferably includes one or more developer components and optionally one or more coupler components. At least one oxidative dye precursor product is especially preferably present in a total amount of from about 0.0001 to about 10.0% by weight, preferably from about 0.001 to about 8% by weight, each based on the weight of composition (A) or (C).

It may be preferable as contemplated herein to select as the developer component at least one compound from the group formed from p-phenylenediamine, p-toluenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N-bis-(2-hydroxyethyl)-N,N-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine as well as their physiologically safe salts.

Preferably at least one developer component is present in a total amount of from about 0.0001 to about 10.0% by weight, preferably from about 0.001 to about 8% by weight, each based on the weight of composition (A).

Coupler components do not by themselves form any significant dyeing as part of oxidative dyeing but instead always require the presence of developer components. It is therefore preferable as contemplated herein for at least one coupler component to be used in addition when using at least one developer component.

Coupler components preferred as contemplated herein are selected from 3-aminophenol, 5-amino-2-methylphenol, n-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, n-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-yl phenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxy-naphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these components or their physiologically safe salts.

At least one coupler component is preferably present in a total amount of from about 0.0001% to about 10.0% by weight, preferably from about 0.001 to about 8% by weight each based on the weight of composition (A) or (C).

Developer components and coupler components are generally used here in approximately equimolar amounts relative to one another. Although equimolar use has also proven expedient, a certain excess of individual oxidative dye precursors is not a disadvantage, so that developer components and coupler components may be present in a molar ratio of about 0.2-2, in particular about 0.5-1.

The direct dyes are preferably the ones already described above. The treatment time is preferably from about 5 to about 60 minutes, in particular from about 5 to about 50 minutes, especially preferably from about 10 to about 45 minutes. During the time of treatment of the fibers by the agents, it may be advantageous to support the lightening or color change process by applying heat. It is also possible for the treatment phase to take place at room temperature. The temperature during the treatment time in particular is between from about 20° C. and about 40° C., in particular between from about 25° C. and about 38° C. The agents already yield good treatment results at physiologically tolerable temperatures of less than about 45° C. After the end of the color change process, all components on the keratin fibers are rinse out of the hair with water or a cleaning agent containing a surfactant. Suitable cleaning agents here may include in particular commercial shampoo, wherein it is then possible to omit the cleaning agent in particular, and the rinsing process may be carried out with tapwater if the color-changing agent has a greater surfactant content.

Another subject matter of the present disclosure is the use of a combination of succinic acid and ethylene carbonate in an agent for changing the color of keratin-containing fibers, in particular human hair, containing at least one oxidizing agent, selected from sodium percarbonates and inorganic salts of a peroxosulfuric acid, as well as mixtures thereof, and additionally at least one chelating agent, selected from the acids mentioned below and/or the alkali metal salts: ethylenediaminetetraacetic acid (EDTA), N-hydroxyethyl-ethylenediaminetriacetic acid, nitrilotriacetic acid, iminodisuccinic acid, N-2-hydroxyethyliminodiacetic acid, ethylene glycol-bis-(β-aminoethyl ether)-N,N-tetraacetic acid, aminotrimethylene phosphonic acid, pentasodium aminotrimethylene phosphonate as well as mixtures thereof in a total amount of from about 0.1 to about 1.4% by weight, preferably from about 0.2 to about 1.4% by weight, especially preferably from about 0.5 to about 1.4% by weight each based on the weight of the hair bleaching agent, to reduce the damage to keratinic fibers in particular human hair which is caused by treatment of these fibers with an oxidative agent to change the color of the keratin-containing fibers, in particular human hair.

What was said about the preferred hair bleaching agents as contemplated herein or agents for changing the color of keratin-containing fibers also applies, mutatis mutandis, to the multicomponent package units (kits of parts) as contemplated herein and preferred as contemplated herein.

What was said above regarding the hair bleaching agents as contemplated herein or agents for changing the color of keratin-containing fibers and those preferred as contemplated herein also applies, mutatis mutandis, to the methods for lightening and/or changing the color of the keratinic fibers as contemplated herein and preferred as contemplated herein.

What was said above about the hair bleaching agents as contemplated herein, or agents for changing the color of keratin-containing fibers and those preferred as contemplated herein also applies, mutatis mutandis, to the use as contemplated herein.

EXAMPLES 1.1 TABLE 1

Composition (A)

| Ingredient | Amount (% by weight) |
| --- | --- |
| Sodium silicate (molar SiO$_2$/Na$_2$O ratio >2.6; ≤3.2) | 27 |
| Magnesium carbonate hydroxide | 13.2 |
| Sodium hexametaphosphate | 0.2 |
| Methyl methacrylate/methacrylic acid copolymer (INCI: Acrylates Copolymer)* | 1.0 |
| Sodium gluconate | 0.003 |
| Sodium chloride | 0.003 |
| Carboxymethyl cellulose (Na salt) | 1.99 |
| Sodium glycolate | 0.004 |
| EDTA-Na$_4$ | 1.352 |
| Hydrophilic silicic acid | 0.61 |
| Potassium peroxodisulfate | 31.68 |
| Potassium sulfate | 0.16 |
| Ammonium sulfate | 0.05 |
| Diammonium peroxodisulfate | 9.9 |
| Liquid paraffin | 3.6 |
| Water | 9.248 |

*A 3% by weight solution of this copolymer in water has a viscosity in the range of 7700 to 11,000 mPas at 20° C.

1.2 TABLE 2

Composition (B)

| Ingredient | Amount (% by weight) |
| --- | --- |
| Sodium benzoate | 0.04 |
| Dipicolinic acid | 0.1 |
| Disodium pyrophosphate | 0.1 |
| Potassium hydroxide | 0.1 |
| Propane-1,2-diol | 0.5 |
| HEDP | 0.15 |
| Liquid paraffin | 2.0 |
| Cetearyl alcohol | 3.6 |
| Ceteareth-20 | 1.2 |
| Hydrogen peroxide | 9.0 |
| Water | to a total of 100 |

1.3 TABLE 3

Composition (D)

| Ingredient | Amount (% by weight) |
| --- | --- |
| Ethylene carbonate | 5 |
| Succinic acid | 5 |
| Water | 90 |

Compositions (A), (B) and (D) are mixed together in a weight ratio (A):(B):(D) of 5:10:1.

2. Application

Strands of hair of the curling natural strand type (7-0) were cleaned and dried. The freshly prepared mixture of the compositions of the hair bleaching agent was applied to the strands of dry hair (5 g application mixture per gram of hair). After a treatment time of 45 minutes at 32° C., the strands were rinsed for 2 minutes with hot tapwater and then air dried. This bleaching process was repeated once so that on the whole the strands of hair were bleached twice in succession.

3. Measurements of the Cysteic Acid Content

To measure the hair damage caused by the hair bleaching, the cysteic acid value of each treated hair strand was determined by quantitative NIR spectroscopy.

The spectra were recorded with an MPA™ FT-NIR spectrometer from Bruker Optik GmbH. The infrared range includes the wavenumber range from 12,500 cm$^{-1}$ to 4000 cm$^{-1}$ and is characteristic of the harmonic and combination vibrations of CH, OH and NH groups, for example.

Measurements were carried out with diffuse reflection on the samples in six different sample positions using the modular integrating sphere concept. For analysis of the measured NIR spectra, the wavenumber range from 7300 cm$^{-1}$ to 4020 cm$^{-1}$ was selected.

The NIR spectra of cystine have characteristic absorption bands in the wavenumber range from 6200 cm$^{-1}$ to 5500 cm$^{-1}$. If hair is altered due to severe damage (i.e., if the cysteic acid content of the hair increases), this affects the bands in the NIR spectrum at 5020 cm$^{-1}$ to 4020 cm$^{-1}$ that are characteristic of cysteic acid. Quantitative analysis of the NIR spectra was performed with computer assistance.

For each hair bleaching method, 18 strands of hair were treated and measured, and the average of each of the 18 measurements was calculated. Comparative Examples V1-V7 have a different acid instead of succinic acid and/or have propylene carbonate instead of ethylene carbonate in composition (D). Example E1 contains succinic acid and ethylene carbonate in composition (D).

TABLE 4

Measurements of the cysteic acid content in keratinic fibers after treatment with various oxidative hair bleaching agents. E1 is an example as contemplated herein; V1 to V7 are comparative examples. Cysteic acid content (mol cysteic acid/100 mol amino acid)

| | 2x hair bleaching with a combination of | | | | | | | |
|---|---|---|---|---|---|---|---|---|
| | Blank sample | | | | | | | |
| | E1 | V1 | V2 | V3 | V4 | V5 | V6 | V7 |
| Meas- | | | | Without combination | | | | |
| ure- | SA + | TA + | LA + | CA + | SA + | TA + | LA + | CA + |
| ment | EC | EC | EC | EC | PC | PC | PC | PC |
| 1 | 6.875 | 5.632 | 6.471 | 5.953 | 6.039 | 6.013 | 5.622 | 6.724 | 6.477 |
| 2 | 7.008 | 6.207 | 6.451 | 6.651 | 6.689 | 6.313 | 6.217 | 6.922 | 6.417 |
| 3 | 6.806 | 6.433 | 6.701 | 5.791 | 6.665 | 6.531 | 6.414 | 6.658 | 6.126 |
| 4 | 6.816 | 6.683 | 6.782 | 6.436 | 6.817 | 6.713 | 6.843 | 7.286 | 6.88 |
| 5 | 6.728 | 5.805 | 6.114 | 6.096 | 5.827 | 6.311 | 6.259 | 6.351 | 6.128 |
| 6 | 7.07 | 6.12 | 6.528 | 6.241 | 6.51 | 6.488 | 6.46 | 6.811 | 6.563 |
| 7 | 7.182 | 6.866 | 6.286 | 6.696 | 6.724 | 7.267 | 6.678 | 7.073 | 6.711 |
| 8 | 6.663 | 6.06 | 5.688 | 6.257 | 6.131 | 6.564 | 6.107 | 6.659 | 6.246 |
| 9 | 7.005 | 6.411 | 6.258 | 6.49 | 6.553 | 6.414 | 6.6 | 6.952 | 6.449 |
| 10 | 7.112 | 6.597 | 6.764 | 6.593 | 6.979 | 7.389 | 6.979 | 7.138 | 7.001 |
| 11 | 6.759 | 6.157 | 7.336 | 7.195 | 6.988 | 6.966 | 6.517 | 7.516 | 6.434 |
| 12 | 6.816 | 6.078 | 6.566 | 5.991 | 6.582 | 6.112 | 6.469 | 6.464 | 6.583 |
| 13 | 6.805 | 6.275 | 6.591 | 5.972 | 6.807 | 6.395 | 6.519 | 6.761 | 6.925 |
| 14 | 7.179 | 6.596 | 7.04 | 6.429 | 7.045 | 6.652 | 6.879 | 7.202 | 7.372 |
| 15 | 6.4 | 6.015 | 6.309 | 5.389 | 5.789 | 5.887 | 6.243 | 6.475 | 6.355 |
| 16 | 6.926 | 6.268 | 6.252 | 5.723 | 6.743 | 6.697 | 6.506 | 6.901 | 6.631 |
| 17 | 7.16 | 7.095 | 6.632 | 6.397 | 6.79 | 6.533 | 6.77 | 6.963 | 6.782 |
| 18 | 6.786 | 6.066 | 6.113 | 5.849 | 6.048 | 6.247 | 6.033 | 6.455 | 6.023 |
| Average | 6.894 | 6.298 | 6.493 | 6.231 | 6.540 | 6.527 | 6.451 | 6.851 | 6.561 |

SA: succinic acid;
TA: tartaric acid;
LA: lactic acid;
CA: citric acid;
EC: ethylene carbonate;
PC: propylene carbonate 4. Measurements of Color Differences All lightened strands of hair were measured using a colorimeter from the X-Right company, "exact" model, and the measured colors were described on the basis of their coordinates in the CIELAB L*, a*, b* color space, where the value L* describes the lightness, the value a* describes the green or red components, and the value b* describes the blue or yellow components of the colors.

The deviation in the color hue of the hair after bleaching in the presence of combinations E1, V1-V7 from the color hue of the hair after bleaching without the addition of acids and alkylene carbonates was calculated on the basis of the distance $\Delta E$ in the L*, a*, b* color space. The distance $\Delta E$ is defined as $\Delta E=[(L^*-L_0)^2+(a^*-a_0)^2+(b^*-b_0)^2]^{0.5}$ where L*, a* and b* are the coordinates of the color hue after bleaching in the presence of a combination E1, V1-V7 and $L_0$, $a_0$ and $b_0$ are the coordinates of the color hue after bleaching without the addition of acids and alkylene carbonates. Color differences of $\Delta E \leq 2$ are not detectable to the untrained eye.

TABLE 5

Deviation in the color hue of the hair after bleaching in the presence of combinations E1, V1-V7 from the color hue of the hair after bleaching without the addition of acids and alkylene carbonates (blank sample)

| | 2x bleaching with the combination of | | | | | | | |
|---|---|---|---|---|---|---|---|---|
| | Blank sample | | | | | | | |
| | E1 | V1 | V2 | V3 | V4 | V5 | V6 | V7 |
| Meas- | | | | Without combination | | | | |
| ure- | SA + | TA + | LA + | CA + | SA + | TA + | LA + | CA + |
| ment | EC | EC | EC | EC | PC | PC | PC | PC |
| CIE L* | 72.22 | 70.74 | 71.75 | 69.25 | 71.87 | 71.96 | 72.08 | 73.06 | 71.55 |
| CIE a* | 4.82 | 4.99 | 4.97 | 5.87 | 4.97 | 4.94 | 4.81 | 4.31 | 4.53 |
| CIE b* | 27.80 | 27.82 | 27.17 | 27.63 | 26.77 | 26.98 | 26.16 | 26.34 | 26.85 |
| $\Delta E$ | 0 | 1.49 | 0.80 | 3.15 | 1.10 | 0.86 | 1.65 | 1.76 | 1.20 |

SA: succinic acid;
TA: tartaric acid;
LA: lactic acid;
CA: citric acid;
EC: ethylene carbonate;
PC: propylene carbonate Only in the case of E1 (example as contemplated herein) is it possible to observe a particularly effective protection of the keratinic fibers in oxidative lightening without a visible color difference in comparison with the blank sample. Although combination V2 of lactic acid and ethylene carbonate exhibits a slightly better protection of hair than the combination as contemplated herein, the hair bleaching result differs visibly from the hair bleaching result obtained on the blank sample ($\Delta E=3.15$) and is much darker than the latter (L* is much lower).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair bleaching agent for oxidative lightening of hair, comprising:
   a) a composition (A) comprising at least one alkalizing agent and at least one persulfate; and
   b) a composition (B) with a pH of from about 2.5 to about 5.5, comprising hydrogen peroxide succinic acid and ethylene carbonate, wherein the succinic acid is from about 0.01% to about 1% by weight, based on a total weight of the hair bleaching agent, and ethylene carbonate is from about 0.01% to about 1% by weight, based on the total weight of the hair bleaching agent; and
   wherein when all the compositions of the hair bleaching agent are mixed together, an alkaline pH is established in the range of from about 8 to about 12; and
   wherein the hair bleaching agent does not contain any composition (C).

2. The hair bleaching agent according to claim 1, wherein the hair bleaching agent comprises about 0% by weight acylpyridinium derivatives.

3. The hair bleaching agent according to claim 1, wherein the weight-based ratio of succinic acid to ethylene carbonate is from about 3:1 to about 1:3.

4. The hair bleaching agent of claim 1 further comprising:
at least one oxidative dye precursor or at least one direct dye.

5. The hair bleaching agent of claim 1 wherein;
when all the compositions of the hair bleaching agent are mixed together, the alkaline pH is in the range of from about 8.5 to about 11.5.

6. The hair bleaching agent of claim 1 wherein:
when all the compositions of the hair bleaching agent are mixed together, the alkaline pH is in the range of from about 9 to about 10.5.

7. The hair bleaching agent of claim 1 wherein:
the composition (B) has a pH of from about 3 to about 5.

8. The hair bleaching agent of claim 1 wherein:
the composition (B) has a pH of from about 3.2 to about 4.

9. A method for oxidative lightening of hair, comprising:
combining all compositions of a hair bleaching agent, wherein the hair bleaching agent comprises a composition (A) comprising at least one alkalizing agent and at least one persulfate; and a composition (B) with a pH of from about 2.5 to about 5.5, comprising hydrogen peroxide, succinic acid and ethylene carbonate and wherein the succinic acid is from about 0.01% to about 1% by weight, based on a total weight of the hair bleaching agent, and ethylene carbonate is from about 0.01% to about 1% by weight, based on the total weight of the hair bleaching agent wherein the hair bleaching agent does not contain any composition (C) and mixing all the compositions of the hair bleaching agent, wherein when all the compositions of the hair bleaching agent are mixed together an alkaline pH in the range of from about 8 to about 12 is established in the hair bleaching agent;

applying the hair bleaching agent to the hair immediately after mixing all the compositions of the hair bleaching agent;

leaving the hair bleaching agent on the hair for from about 5 to about 60 minutes; and rinsing the hair with water; and optionally washing the hair with a cleaning agent comprising a surfactant.

10. The method of claim 9 wherein:
composition (B) has a pH of from about 3 to about 5.

* * * * *